United States Patent
Edwards et al.

(10) Patent No.: US 11,062,238 B2
(45) Date of Patent: *Jul. 13, 2021

(54) RECREATING A TIME-ORDERED SEQUENCE OF EVENTS

(71) Applicant: CERNER INNOVATION, INC., Lenexa, KS (US)

(72) Inventors: David Lee Edwards, Kansas City, MO (US); Ryan Alan Brush, Overland Park, KS (US)

(73) Assignee: CERNER INNOVATION, INC., Lenexa, KS (US)

( * ) Notice: Subject to any disclaimer, the term of this patent is extended or adjusted under 35 U.S.C. 154(b) by 919 days.

This patent is subject to a terminal disclaimer.

(21) Appl. No.: 13/663,732

(22) Filed: Oct. 30, 2012

(65) Prior Publication Data

US 2013/0054262 A1    Feb. 28, 2013

Related U.S. Application Data

(63) Continuation-in-part of application No. 13/207,777, filed on Aug. 11, 2011.

(51) Int. Cl.
  *G16H 10/20* (2018.01)
  *G16H 10/40* (2018.01)
  *G16H 20/10* (2018.01)
  *G06Q 10/06* (2012.01)

(52) U.S. Cl.
  CPC ............ *G06Q 10/06* (2013.01); *G16H 10/20* (2018.01); *G16H 10/40* (2018.01); *G16H 20/10* (2018.01)

(58) Field of Classification Search
  CPC ........ G06Q 10/06; G16H 10/40; G16H 10/20; G16H 20/10
  USPC ............................................................ 705/3
  See application file for complete search history.

(56) References Cited

U.S. PATENT DOCUMENTS

| | | |
|---|---|---|
| 6,468,210 B1 * | 10/2002 | Iliff .............................. 600/300 |
| 2002/0091548 A1 * | 7/2002 | Auer ..................... G06F 19/322 705/3 |
| 2008/0215367 A1 * | 9/2008 | Marshall .......................... 705/3 |
| 2010/0261977 A1 | 10/2010 | Seeley |

OTHER PUBLICATIONS

Pre-Interview First Action Interview in U.S. Appl. No. 13/207,777 dated Jun. 7, 2013, 4 pages.

(Continued)

*Primary Examiner* — Hiep V Nguyen
(74) *Attorney, Agent, or Firm* — Shook, Hardy & Bacon, LLP

(57) ABSTRACT

A method, system and medium are provided for enabling re-creation of a time-ordered sequence of clinical data. Sets of data elements for a patient are received in sequence from a clinical system, and for each data element a time stamp is attached. For any given set of data elements, a maximum time stamp is determined, implying that all events in a clinical system resulting in modifications to data elements contained in the set occurred on or before the maximum time stamp. A subsequent retrieval from a clinical system yields a set of data elements in which the time stamp for each data element occurs after the maximum time stamp from the previous set.

20 Claims, 9 Drawing Sheets

(56) References Cited

OTHER PUBLICATIONS

First Action Interview Office Action in U.S. Appl. No. 13/207,777 dated Aug. 7, 2013, 5 pages.
Non-Final Office Action dated Jul. 23, 2014 in U.S. Appl. No. 13/207,777, 13 pages.
Final Office Action dated Feb. 1, 2016 in U.S. Appl. No. 13/207,777, 17 pages.
Non-Final Office Action dated Aug. 12, 2015 in U.S. Appl. No. 13/207,777, 16 pages.
Final Office Action in U.S. Appl. No. 13/207,777, dated Oct. 29, 2013.

* cited by examiner

300

| EVENT HISTORY | | |
|---|---|---|
| DOE, JOHN | | 🔍 SEARCH |
| DATE/TIME | EVENT | CONTEXT |
| 302 — 4/13/11 15:22:44 | MED ALERT 4 | DETAILS |
| 302 — 4/13/11 15:17:21 | MED ALERT 3 | DETAILS |
| 302 — 4/13/11 15:07:59 | MED ALERT 2 | DETAILS |
| 302 — 4/13/11 14:58:04 | MED ALERT 1 | DETAILS |
| 304   306 | | 308 |

*FIG. 3.*

500 — EVENT DETAILS – MED ALERT 1 FOR JOHN DOE, 4/13/11

DOE, JOHN  
ITEMS TRIGGERING MED ALERT 1  
504 — RULE VERSION 1.1.23

🔍 SEARCH

| TYPE | VALUE | INTERPRETATION |
|---|---|---|
| 502 — LAB RESULT 1 | 100 | HIGH |
| 502 — LAB RESULT 2 | 4.3 | LOW      508 |
| 502 — DIAGNOSIS 1 | <DIAGNOSIS TEXT> | VIEW CLINICAL NOTE |
| 506 — REF. INFO. | <REF. TEXT> | LINK TO REF. |

*FIG. 5.*

RECREATING A TIME-ORDERED SEQUENCE OF EVENTS

CROSS-REFERENCE INFORMATION

This application is a continuation-in-part application of pending U.S. patent application Ser. No. 13/207,777, filed Aug. 11, 2011, entitled "Recreating the State of a Clinical System." The entirety of the aforementioned patent application is incorporated by reference herein.

SUMMARY

Embodiments of the invention are defined by the claims below, not this summary. A high-level overview of various aspects of the invention are provided here for that reason, to provide an overview of the disclosure, and to introduce a selection of concepts that are further described in the Detailed-Description section below. This summary is not intended to identify key features or essential features of the claimed subject matter, nor is it intended to be used as an aid in isolation to determine the scope of the claimed subject matter. In brief and at a high level, this disclosure describes, among other things, ways to recreate the state of a system as it existed at a prior point in time and ways to recreate a time-ordered sequence of data elements.

In embodiments of the invention, data elements collected in the course of caring for a patient are stored with a time stamp. Additional data associated with the patient data and with a clinical system generally are also collected and stored in a way that enables correlation of the additional data with a time when it was used or was valid. The additional data includes, for example, functions used to calculate derived data elements or to trigger alert conditions. And the additional data includes reference information that is useable to inform the functions.

As such, a time occurring in the past at which to recreate the state of the clinical system may be selected. Corresponding patient data and additional data are identified based on their respective time stamps. The state of the clinical system is thus recreated in a way that shows the user only the data that was available to the system at the selected time. And the state includes the additional data in the condition that it existed at the selected time, e.g. functions and reference information are provided in the versions that were available at the selected time. Thereby, the clinical system may be audited or otherwise reviewed to determine why or how events occurred, or did not occur, at the selected time based on an accurate representation of the state of the system as it existed at the selected time.

In other embodiments of the invention, sets of data elements for a given patient are received in a sequential manner from a clinical system. A set of data elements belongs to one or more clinical domains, and for each data element, a time stamp is attached. For a given set of data elements received from the clinical system, a maximum time stamp can be determined. This implies that all events in the clinical system resulting in modifications to data elements contained in this set occurred on or before the maximum time stamp. A subsequent retrieval from the clinical system yields a set of data elements in which the time stamp for each data element occurs after the maximum time stamp from the previous set. A time-ordered sequence of data elements is recreated by concatenating each set of data elements retrieved in sequence from the clinical system. The result is a comprehensive and time-ordered view of the data elements, which is important in, for example, surveillance systems such as antibiotic or sepsis surveillance systems.

DESCRIPTION OF THE DRAWINGS

Illustrative embodiments of the invention are described in detail below with reference to the attached drawing figures, and wherein:

FIG. 3 is a graphical representation of an event-history window of a user interface in accordance with an embodiment of the invention;

FIG. 5 is a graphical representation of an event-details window of a user interface in accordance with an embodiment of the invention;

DETAILED DESCRIPTION

Figure 1:
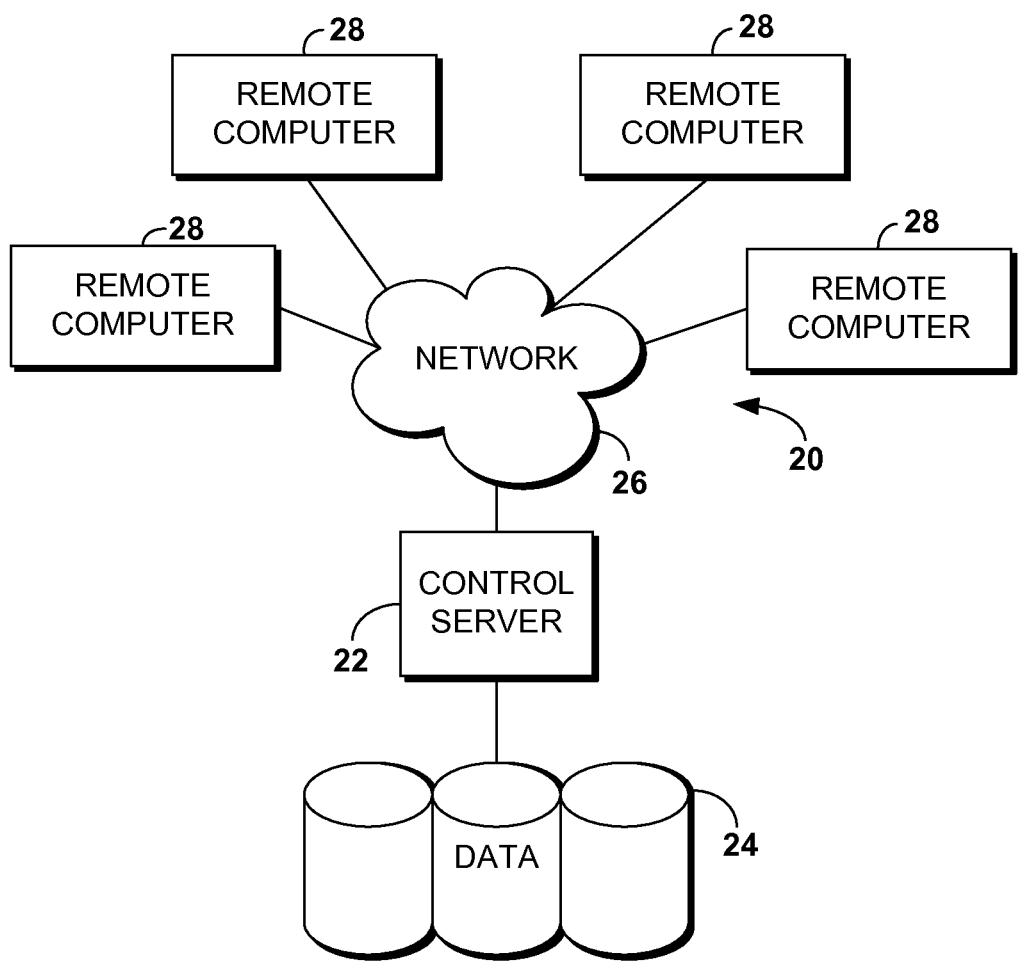
FIG. 1 is a block diagram depicting an exemplary computing environment suitable for use in accordance with an embodiment of the invention.

The subject matter of select embodiments of the invention is described with specificity herein to meet statutory requirements. But the description itself is not intended to necessarily limit the scope of claims. Rather, the claimed subject matter might be embodied in other ways to include different steps or combinations of steps similar to the ones described in this document, in conjunction with other present or future technologies. Terms should not be interpreted as implying any particular order among or between various steps herein disclosed unless and except when the order of individual steps is explicitly described.

Embodiments of the invention provide systems, methods and computer-readable media for recreating the state of a system as it existed at selected time in the past. Further embodiments of the invention provide systems, methods, and computer-readable media for generating a time-ordered sequence of clinical data elements. As described herein, time uses any temporal measurement or logical sequencing. The time is measurable by any desired means and in any units. The notion of time might be that time is measureable based on a clock, a counter, or any other logical sequencing of events. For example, time might comprise a particular time of day measured based on Coordinated Universal Time (UTC) or Greenwich Mean Time (GMT) like 5:30 PM, a time and date (e.g. Mar. 28, 2011 17:30:00). The time might also comprise a point in a sequence of events or a counter, such as a computer's system time that is based on the number of seconds that have elapsed since Jan. 1, 1970 00:00:00 Universal Time.

The system for which the state is recreated is described herein as a clinical system, such as that of a hospital or medical facility. The clinical system may comprise an electronic medical record system associated with a hospital or medical facility. Clinical systems associated with different hospitals or medical facilities may be disparate in nature; that is, the clinical systems may store data elements in different ways. But embodiments of the invention are applicable to any computing system for which it is desirable to enable recreation of a prior state. Such computing systems include, for example and not limitation, those used for financial transactions, insurance claims, manufacturing or the like.

As described herein, the state of a system is recreated at a selected time—the selected time occurring in the past. The state of the system is descriptive of the knowledge available to the system at a given time. In an embodiment, the knowledge available to the system includes part or all of the data stored in memory components of the system, or that are accessible by the system, at the given time. The state of the system changes any time there is a mutation of data. Mutation of data includes additions of new data as well as modifications and deletions of existing data. For example, the state of a system that includes data elements X, Y and Z at a time (t) and that receives a new data element A at a time (t+1) has been changed by the addition of the new data element A. Thus, at time (t) the state of the system includes data elements X, Y and Z while the state of the system at time (t+1) includes data elements X, Y, Z and A.

Embodiments of the invention are adapted to allow recreation of states of systems that employ functions and/or reference information to manipulate data elements. Functions, as described herein, include any available manipulator of data elements including, for example and not limitation, mathematical functions and program routines. Reference information, as described herein, includes any available information used by a system that informs, instructs or describes a function or data element. For example, reference information might describe a range of values of a data element that are useable in a function or what a value of a data element means or a name of a data element. For instance, in a clinical setting, reference information might describe any aspect of a body-mass index (BMI) calculation. The reference information might describe data elements that are used for the BMI calculation, ranges of values that might result from the BMI calculation, what a value means when it falls within one of the ranges and might identify the function to be used for the BMI calculation.

Functions and reference information employed by a system may change or be updated from time to time. Thus, a function that is used at a time (t) may not be the same as a function that is currently in use or that is used at any time before or after the time (t). Such changes may alter the resulting data that is produced by the function or through use of the reference information. Prior systems are unable to easily account for these changes or to track their occurrence. And accurate recreation of the state of a system requires knowledge of the data elements, functions and reference information available at the time selected for recreation of the state. For example, when a function is modified between a current time and a selected time for state recreation, without knowledge of the modification and of the previous form of the function, the state of the system may be difficult or impossible to accurately recreate, e.g. the current function may result in a different outcome than the previous function that was in use at the selected time.

These changes to functions and reference information are described herein as updates of the function or reference information to a new version. A function that is updated is therefore changed from a first version to a second version.

In an embodiment of the invention, the functions used by the system are pure functions that have referential transparency. Pure functions are known as functions that do not change or modify existing data elements, i.e. functions that do not have side effects. And referential transparency indicates that a function can be replaced by its product. Use of pure functions enables re-creation of the state of the system because the values of data elements used by the functions are identifiable. If the functions altered the data elements then the values of the data elements that existed at a selected time, prior to initial execution of the function, would be difficult or impossible to identify; subsequent re-execution of the functions based on the changed data elements would thus result in a different value than what would have resulted in the initial execution.

Pure functions also enable re-execution and analysis of the behavior of the functions at a later time. For instance, if a function causes an alert to be issued at a time (t), the use of pure functions enable the logic that triggered the alert to be re-executed at any future time, and to answer, without ambiguity, why that alert was issued at the time (t). This removes the need for detailed auditing to determine why an alert was issued. And this aids analysis of the functions, inputs, and outputs thereof that might lead to improvements in the quality of the functions and the outputs or alerts issued thereby.

Embodiments of the invention are further adapted to recreate a time-ordered sequence of data elements. As mentioned above, data elements may undergo mutations including the addition of a data element, and/or the modification or deletion of an existing data element. Capturing and ordering the sequence of these changes using time stamps is important in generating a complete, comprehensive view of the clinical system. Traditional data feeds, such as HL-7 feeds, fail to capture the temporal relationships between state changes and, instead, simply extract data that has changed since the feed connection was installed. Because the temporal relationships between state changes is not accounted for, processing of data elements received from traditional feeds must occur in the order the data was received (e.g., serial processing). In other words, the utilization of parallel processing using data received from traditional feeds is limited because it is not possible to recreate the temporal order of the data elements.

In an embodiment, computer-readable media having computer-executable instructions embodied thereon that, when executed, perform a method for recreating a state of a system at a prior time is described. The method includes storing data elements for a patient with a respective time stamp. An indication of functions and pieces of reference information associated with the data elements is also stored. A selection of a time (t) that occurs in the past is received. A first subset of the data elements for the patient that include the time stamp occurring at or before the time (t) is identified. A second subset of the functions and the pieces of reference information associated with the first subset is also identified. A state of the system at the time (t) is recreated based on the first subset and the second subset.

In another embodiment, a computer-implemented method for auditing a computing system to identify conditions of the computing system existing at a selected prior time is described. A log of state changes that occur for data elements, functions and reference materials associated with a patient is generated. The log indicates a time at which each of the state changes occurred. A selection of a time (t) is received. A subset of the data elements that were known to a computing system at or before the time (t) is identified based on the log and/or an indication stored with each of the data elements that shows a time that the respective data element was received. Functions that were in use by the computing system at the time (t) are determined based at least partially on the log. A user interface that depicts a state of the computing system at the time (t) based on the subset of the data elements and the functions is generated.

In another embodiment, a system for tracking data associated with a patient is described. The system includes a patient-data-tracking component, a knowledge-base-tracking component, a function-tracking component and an auditing component. The patient-data-tracking component is configured to store data elements associated with a patient and to associate a respective time stamp with each of the data elements. The knowledge-base-tracking component is configured to identify a version of a piece of reference information associated with the data elements. The function-tracking component is configured to identify a version of a function associated with the data elements. And the auditing component is configured to recreate a state of the system as it existed at a selected time (t) by receiving a selection of the time (t), identifying one or more of the data elements that include a respective time stamp that occurs at or before the time (t), and identifying the versions of the piece of reference information and the function.

In a further embodiment, computer-readable media having computer-executable instruction embodied thereon that, when executed, perform a method for producing a time-ordered sequence of data elements is described. The method comprises receiving ongoing sets of data elements in sequence, each with an associated time stamp, for a patient from a clinical system. For any given set of data elements, a maximum time stamp is determined. Once the initial set of data elements is received, all subsequent retrievals use the maximum time stamp determined from the prior set of data elements in deciding which data elements are contained in the resulting set. The concatenation of the sets of data forms a time-ordered sequence of data elements in the clinical system.

In an additional embodiment, a system for generating a time-ordered sequence of data elements associated with a patient is described. The system comprises a patient-data-tracking component configured to identify a plurality of sets of data elements associated with the patient and to associate a respective time stamp with each of the data elements in the plurality of sets of data elements. The system further comprises a knowledge-base-tracking component configured to identify a maximum time stamp associated with each set of data elements of the plurality of sets of data elements. The system also comprises an auditing component configured to recreate a time-ordered sequence of data elements by concatenating the plurality of sets of data elements such that each subsequent set of data elements includes a respective time stamp that occurs after the respective maximum time stamp associated with the previous set of data elements.

In yet another embodiment, a computer-implemented method for recreating a time-ordered sequence of data elements is described. The method comprises at a first point in time, receiving from a clinical system a first set of data elements for a patient, wherein each data element in the first set of data elements has undergone one or more state changes, and wherein each data element in the first set of data elements is associated with a time stamp. A maximum time stamp of the first set of data elements is determined. At a second point in time, the maximum time stamp is used to identify in the clinical system a second set of data elements for the patient. Each data element in the second set of data elements has a respective time stamp after the maximum time stamp of the first set of data elements. A time-ordered sequence of data elements is recreated by concatenating the first and second sets of data elements.

Having briefly described embodiments of the present invention, an exemplary operating environment suitable for use in implementing embodiments of the present invention is described below. Referring to the drawings in general, and initially to FIG. 1 in particular, an exemplary computing system environment, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, personal digital assistants, network PCs, minicomputers, mainframe computers, distributed computing environments that include any of the above-mentioned systems or devices and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus and Peripheral Component Interconnect (PCI) bus, also known as Mezzanine bus.

The control server 22 typically includes therein, or has access to, a variety of computer-readable media and/or communications media, for instance, database cluster 24. Computer-readable media can be any available media that may be accessed by server 22 and includes volatile and nonvolatile media as well as removable and non-removable media. But computer-readable media is exclusive of communications media.

By way of example, and not limitation, computer-readable media include computer storage media and computer storage devices. Computer storage media may include, without limitation, volatile and nonvolatile media as well as removable and non-removable media implemented in any method or technology for storage of information, such as computer-readable instructions, data structures, program modules or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage or other magnetic storage device or any other medium which can be used to store the desired information and which may be accessed by the control server 22.

By way of example, and not limitation, communication media includes wired media such as a wired network or direct-wired connection, and wireless media such as acoustic, RF, infrared and other wireless media. And communications media is inclusive of signals, carrier waves and the like.

The computer storage media discussed above and illustrated in FIG. 1, including database cluster 24, provide storage of computer-readable instructions, data structures, program modules and other data for the control server 22. The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students and the like. The remote computers 28 may also be physically located in non-traditional medical care environments so that the entire health care community may be capable of integration on the network. The remote computers 28 may be personal computers, servers, routers, network PCs, peer devices, other common network nodes or the like, and may include some or all of the elements described above in relation to the control server 22.

Exemplary computer networks 26 may include, without limitation, local area networks (LANs) and/or wide area networks (WANs). Such networking environments are commonplace in offices, enterprise-wide computer networks, intranets and the Internet. When utilized in a WAN networking environment, the control server 22 may include a modem or other means for establishing communications over the WAN, such as the Internet. In a networked environment, program modules or portions thereof may be stored in association with the control server 22, the database cluster 24 or any of the remote computers 28. For example, and not by way of limitation, various application programs may reside on the memory associated with any one or more of the remote computers 28. It will be appreciated that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball or a touch pad. Other input devices may include, without limitation, microphones, satellite dishes, scanners or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, it is appreciated that such components and their interconnection are well known. Accordingly, additional details concerning the internal construction of the control server 22 and the remote computers 28 are not further disclosed herein.

Figure 2:
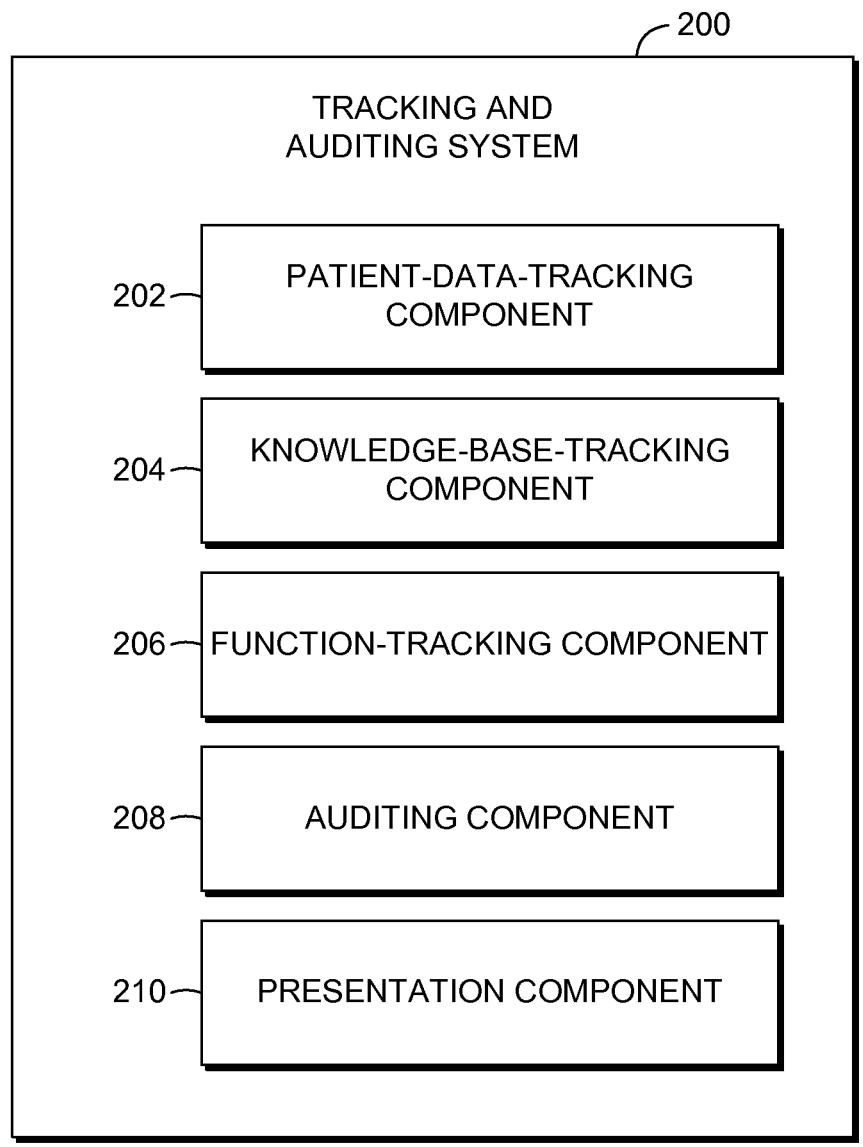
FIG. 2 is a block diagram depicting an system for tracking data associated with a patient in accordance with an embodiment of the invention.

With reference now to FIG. 2, a system 200 for tracking data associated with a patient in accordance with an embodiment of the invention is described. The system 200 includes a patient-data-tracking component 202, a knowledge-base tracking component 204, a function-tracking component 206, an auditing component 208 and a presentation component 210. The patient-data-tracking component 202 is configured to receive and/or collect a plurality of data elements from a variety of sources associated with a clinical computing environment. The sources may include electronic medical record systems associated with hospitals or healthcare facilities. Further, the electronic medical record systems may be disparate in nature (i.e., the electronic medical record systems may store electronic data in different formats or structures). The data elements include any data collected for a patient like, for example, demographic data, contact information, vital signs, symptoms, diagnosis, medical records, and insurance information among others. The data elements also include any derived data. In one aspect, the data elements collected for the patient may belong to a clinical domain such as, for example, clinical documents, lab values, problem lists, medications, orders, and the like. Each clinical domain is represented by a model that represents a logical representation of the data within the clinical domain.

Derived data includes data elements that are the product of one or more functions or the application of reference information. As described previously, a function is any manipulator of one or more data elements. Derived data may thus comprise the product of one or more mathematical equations. Or the derived data might be the product of a computer program or routine that employs one or more data elements, functions and pieces of reference information to determine the derived data. For example, taking the above BMI calculation example, the derived data includes a calculated BMI value as well as an "obese" label that is identified using the calculated BMI and consulting reference information that provides clinical labels for various ranges of BMI. The derived data might also include a numeric label that is associated with the diagnosis, "obese" among a variety of other derived data elements.

A time stamp is provided by the patient-data-tracking component 202 for the data elements, including any derived data elements. A respective time stamp may be provided with each data element or a number of data elements might be associated with a given time stamp. Further, a particular data element may comprise a series of state changes (e.g., addition, modification, deletion, and the like). Each of the state changes is associated with a time stamp. The time stamp indicates a time (e.g., a temporal time or a logical sequencing) when the data element was received, collected, stored, calculated, modified or otherwise acted on by the system 200. The time stamp may be embedded in the data element as metadata. In an embodiment, the time stamp is additionally or alternatively provided via a log file that records modifications of the data elements. Various other ways of tracking modifications of data elements may be employed in embodiments of the invention and are understood as being within the scope of the embodiments described herein.

In an embodiment, when a modification of a data element is received, a modified version of the data element is stored with a time stamp indicating the time at which the modification was made. And the original data element remains in storage—unchanged—with its original time stamp. Thus, both an original and a modified version of the data element are stored by the patient-data-tracking component 202 along with their respective time stamps. In an embodiment, only the modified version of a data element is stored. But the modified version of the data element includes an indication of the mutations made to the previous data element to produce the modified version of the data element.

The data elements stored by the patient-data-tracking component 202 may also include any data associated with the clinical computing environment that may or may not be directly associated with the patient. Such data elements might be associated with other patients, staff, facilities, workflows, computing systems, procedures or the like. In such an instance, data privacy and security procedures are implemented to insure privacy of patient information.

In one aspect, the patient-data-tracking component 202 comprises an extractor that is configured to query one or more clinical systems, extract data elements belonging to a clinical domain, and map a set of time stamps to the data elements in the clinical domain. The patient-data-tracking component may be invoked at preset intervals by, for example, a scheduling component (not shown). The preset intervals may be based on how often the data elements generally are modified. For instance, the patient-data-tracking component 202 may be invoked at short intervals (e.g., seconds to minutes) for data elements that frequently change, or longer intervals (e.g., days to weeks) for data elements that change infrequently.

In one aspect, the patient-data-tracking component 202 may be executed by the following function: D={V, T, extract: T→V}. V is the set of all possible data elements in the domain, D. Since V represents the set of all possible data elements, the domain D usually contains a subset of V. In a normal system, these data elements are modified or mutated as time progresses. As such, $V_t$ is defined as the subset of data elements in V at time t.

Continuing, T is the range of values that represents the notion of a time stamp. The representation of T is completely arbitrary so long as it defines a total ordering either through temporal relatedness or a logical sequencing. Since time stamps from T are associated with data elements in V, a function, timestamp: V→T, can be defined which returns a time stamp for any given data element. Therefore, given two data elements $v_x$ and $v_y$, if time stamp $(v_x)$<time stamp $(v_y)$, then $v_x$ happens before $v_y$.

The function, extract: T→V, implements the algorithm necessary to produce a continuous, time-ordered stream of data elements undergoing state changes in the domain, D. As data elements in V mutate—addition, modification, and removal—new time stamps are associated with those state changes to reflect the temporal relation with prior state changes. As such, the purpose of the extract function is to return the set of data elements that have changed since a given time stamp; this given time stamp is provided as input to the function. The extract function may be carried out by the patient-data-tracking component 202 at an initial time, $T_0$, to yield a snapshot of the entire set of data elements in domain, D. $T_0$ can be seen as the beginning of time in relation to how D defines T. Thus, extracting data elements that have changed since the beginning of time will return all data elements know to D at the time extract $(T_0)$ was invoked. The set of data elements returned by the extract function is dependent upon the time at which the function is invoked. This time is a physical time as measured by an independent clock.

With continued reference to FIG. 2, the knowledge-base-tracking component 204 is configured to track and store reference information that is utilized in the clinical computing environment. The reference information includes any publications, procedures, guidelines or references that are usable in the care of a patient, the processing of the patient's information in the clinical computing environment or any other aspect of manipulation of data elements associated with the patient or the clinical system. For instance, the reference information might include a chart that indicates ranges of a patient's BMI that indicate that the patient is "underweight," in "normal" range, "overweight" or "obese." The reference information might also indicate which function is to be applied based on the age, gender, ethnicity or body type of the patient as well as subdivisions of the major categories and intervention procedures to be prescribed based thereon.

The knowledge-base-tracking component 204 also tracks the version of the reference information that is associated with the one or more data elements. The version of the reference information is tracked by providing an indication in a log file that identifies a time when the version of the reference information updated, i.e. when the reference information is modified. In an embodiment, a pointer is stored with a data element that is associated with a piece of reference information to indicate the version of the reference information that was used in association with the data element. Additionally, both the original and the modified versions of the reference information are stored such that either version may be referenced or used at a later time. Or only the modified version is stored along with an indication of the modifications made to the previous version. Various other ways of tracking modifications to reference information may be employed in embodiments of the invention and are understood as being within the scope of the embodiments described herein.

The knowledge-base-tracking component 204 is further configured to identify a maximum value of a time stamp for a particular set of data elements. As mentioned, data elements may undergo a series of state changes, and each of the state changes is associated with a respective time stamp. The knowledge-base-tracking component 204 is configured to identify the time stamp associated with the most recent state change; this time stamp is the maximum time stamp for the particular set of data elements. Again, the most recent state change may comprise the most recent state change from a temporal aspect or a logical sequencing aspect. The maximum value time stamp is used as input to the extract function defined above.

Thus, the following steps may be carried out by the system 200: (1) $T_0$ is assigned to the time stamp, t, at which extraction will begin. The first extraction phase may be referred to as a historical extraction since it has the effect of fetching a snapshot of all data elements in domain, D; (2) let W=extract(t), where W is the set of data elements that have changed since time stamp, $T_0$. For any data element, v, in W, the timestamp(v)>$T_0$; (3) let t=max_timestamp(W), where max_timestamp is a function returning the largest value of timestamp(v) for every data element, v, in W. This function is choosing the largest time stamp of all data elements in W as input to the next invocation of the extract function; and (4) dispatch W to an application layer for processing. The steps (2) through (4) are repeated indefinitely to produce sets of data elements, $W_0, \ldots W_n$. These sets are used by the auditing component 208 to recreate a time-ordered sequence of data elements.

The function-tracking component 206 is configured to track and store functions employed in the clinical computing environment. As described previously, the functions include any manipulator of one or more data elements, e.g. mathematical functions, computer programs and routines, or the like. The function-tracking component 206 stores functions employed in the care of a patient as well as any other functions that are associated with the patient or the clinical computing system generally.

The function-tracking component 206 also tracks modifications to any of the functions, e.g. versions of the functions. An indication of a modification to a function is placed in a log file. The indication provides a time of the modification and may indicate what the modification was. In an embodiment, the function-tracking component 206 stores an indication of a version of the function that is associated with one or more data elements with the respective data elements. The data elements may be data elements used as variables in the function or may be derived data elements that resulted from execution of the function. In an embodiment both a modified version and an original version of a function is stored or the modified version is stored with an indication of the modifications made thereto. Various other ways of tracking modifications to functions may be employed in embodiments of the invention and are understood as being within the scope of the embodiments described herein.

The auditing component 208 is configured to recreate a state of the clinical computing environment or a portion thereof at a selected time. The computing environment is recreated based on all data, functions and reference information available and/or used in the course of caring for a patient. In an embodiment, the computing environment is recreated based on all data, functions and reference information available to all or part of the computing environment at large. As such, the state of the computing environment is recreated with respect to an individual patient, a plurality of patients or for all or part of a healthcare system.

Figure 4:
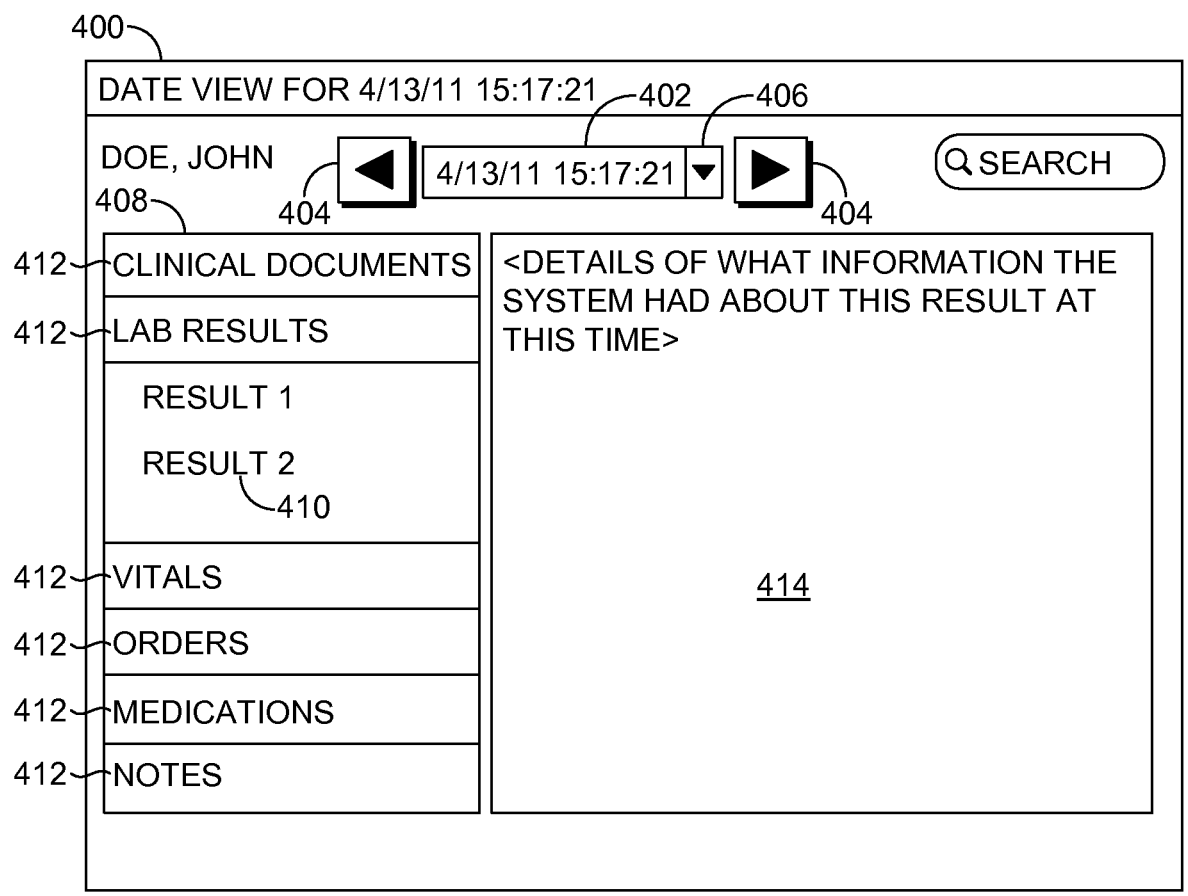
FIG. 4 is a graphical representation of a data-view window of a user interface in accordance with an embodiment of the invention.

The auditing component 208 receives a selection of a time that is prior to a current time at which to recreate the state of the computing environment. The selection of time is received via a user interface like, for example, a user interface 300, 400, 500 depicted in FIGS. 3-5. The time might be selected through manual entry of a time and date into a data field 402 in a data-view pane 400 of the user interface. The time might also be selected by, for example, first selecting a patient from a list of patients or by accessing the system 200 and/or the auditing component 208 via a patient's electronic medical record. Events 302 occurring in the course of treatment of the patient and their associated times might then be displayed in an event-history pane 300 as depicted in FIG. 4. The time is thereby selectable via a respective link 304 in the event history pane 400. A variety of other ways of receiving a selection of a time may be employed in embodiments of the invention and are understood as being within the scope of the embodiments described herein.

The auditing component 208 identifies data elements, such as those stored by the patient-data-tracking component 202, that include or are associated with a time stamp that occurs at or before the selected time, e.g. time stamp≤selected time. Functions and reference information are also identified that are associated with a time stamp occurring prior to the selected time, e.g. time stamp<selected time. In an embodiment, versions of the functions and reference information that are associated with, or that were in use at the selected time are identified.

For example, a function might have been updated to a new version between the selected time and the current time. Thus, a version of the function that was in use at the selected time is identified—not the current version. In an embodiment, only the current version of the function is stored and includes an indication of changes made to a prior version of the function to form the current version. In this instance, the current version is "unmodified" using the indication of the changes in order to identify the function in the form that was in use at the selected time.

The auditing component 208 is further configured to recreate a time-ordered sequence of data elements by concatenating the sets of data elements $W_0, \ldots, W_n$, described above to generate a time-ordered sequence of data elements. The auditing component 208 may communicate the time-ordered sequence of data elements to one or more clinical applications for processing. Because the data elements are associated with respective time stamps, parallel processing may be utilized by the applications to quickly process the data elements while maintaining temporal relatedness between the data elements.

The presentation component 210 is configured to provide a user interface, such as a user interface comprised of windows 300, 400, 500 depicted in FIGS. 3-5, for presentation to a user via a display device. The user interface displays one or more of the identified data elements and may include one or more of the identified functions and pieces of reference information. The data elements, functions and reference information are displayed in any desired form and organization. One such exemplary form is depicted in FIGS. 3-5. The windows 300, 400 and 500 depicted in FIGS. 3-5 are provided herein for exemplary purposes only and are not intended to limit embodiments of the invention in any manner. It is understood that various other configurations of the windows 300, 400 and 500 and the user interface generally may be available and all such configurations are within the scope of the descriptions provided herein.

The system 200 may further comprise a checkpoint component (not shown). The checkpoint component periodically takes a snapshot of where the system 200 is in relation to the extraction process. If a system failure occurs, the process can restart at the previous checkpoint. Further, because time stamps have been associated with the data elements, the system 200 is able to recognize if the data element has previously been processed. In other words, the use of time stamps enables the detection of duplicate data elements.

FIG. 3 depicts the event-history window 300 of an exemplary user interface. The event-history window 300 includes a listing of events 302 that occurred in the course of treatment of a fictional patient "John Doe" along with a respective time 306 associated with each event 302 and a link 308 to details associated with the respective event 302. In the embodiment depicted, the display of the time 306 also serves as the link 304 to provide selection of a time for re-creation of the state of the system, as described previously. In an embodiment, the link 308 also serves as a way of providing a selection of a time for re-creation of the state of the system, the time being the time 306 associated with the event 302. It is recognized that additional and/or alternative data elements might also be provided in the event-history window 300. Such embodiments are understood as being within the scope of the description provided herein.

In an embodiment, selection of link 304 directs the user interface to the data-view window 400 depicted in FIG. 4. In another embodiment, selection of the link 308 directs the user interface to an event-details window 500, as depicted in FIG. 5. The data-view window 400 and the event-details window 500 might also be independently accessible without the use of the event-history window 300.

The data-view window 400 includes the data field 402 in which a selected time might be entered. The data-field 402 might also display a previously selected time or a time associated with an event 302 occurring in the course of treatment of the patient. Selectable icons 404 are provided to allow a user to sequentially scroll through a plurality of events 302 and/or a drop-down icon 406 is provided to provide a drop-down listing of selectable events.

The data-view window 400 also includes a data-selection pane 408 in which a selectable reference 410 to one or more of the data elements, functions and pieces of reference information is provided. The data-selection pane 408 is organized in any desired manner. In the depicted data-selection pane 408, the data elements, functions and/or reference information are organized by headings 412 that are selectable to reveal a listing of the references 410 to the associated data elements, functions and/or pieces of reference information. Selection of the reference 410 causes one or more of the data elements, functions and/or pieces of reference information to be presented in a display pane 414. As such, the data-view window 400 displays the data elements, functions, and reference information that were available at or before a selected time displayed in the data field 402.

The event-details window 500, depicted in FIG. 5, includes one or more data elements 502, functions 504 and/or pieces of reference information 506, or indications thereof, that are associated with a selected event 302. The listing of one or more of the data elements 502, functions 504 and/or pieces of reference information 506 might also comprise a link, such as a link 508, that directs the user interface to present additional related data. As such, in an embodiment, the event-details window 500 provides an indication of the functions 504 related to an event 302 and the data elements 502, pieces of reference information 506, and/or additional functions that were used as variables in the function 504 that resulted in the event 302.

For example, in an embodiment, the event 302 is an alert that is triggered to notify clinicians of a potential condition of the fictional patient "John Doe." The alert is triggered by execution of the function 504 resulting in a predetermined value associated with the condition. For instance, the function might be a BMI calculation and the alert is triggered when a calculated BMI falls in the "obese" range. Thus, the event-details window 500 displays the version of the BMI function and any data elements, pieces of reference information and/or other functions used to produce the BMI value that triggered the alert.

Figure 6:
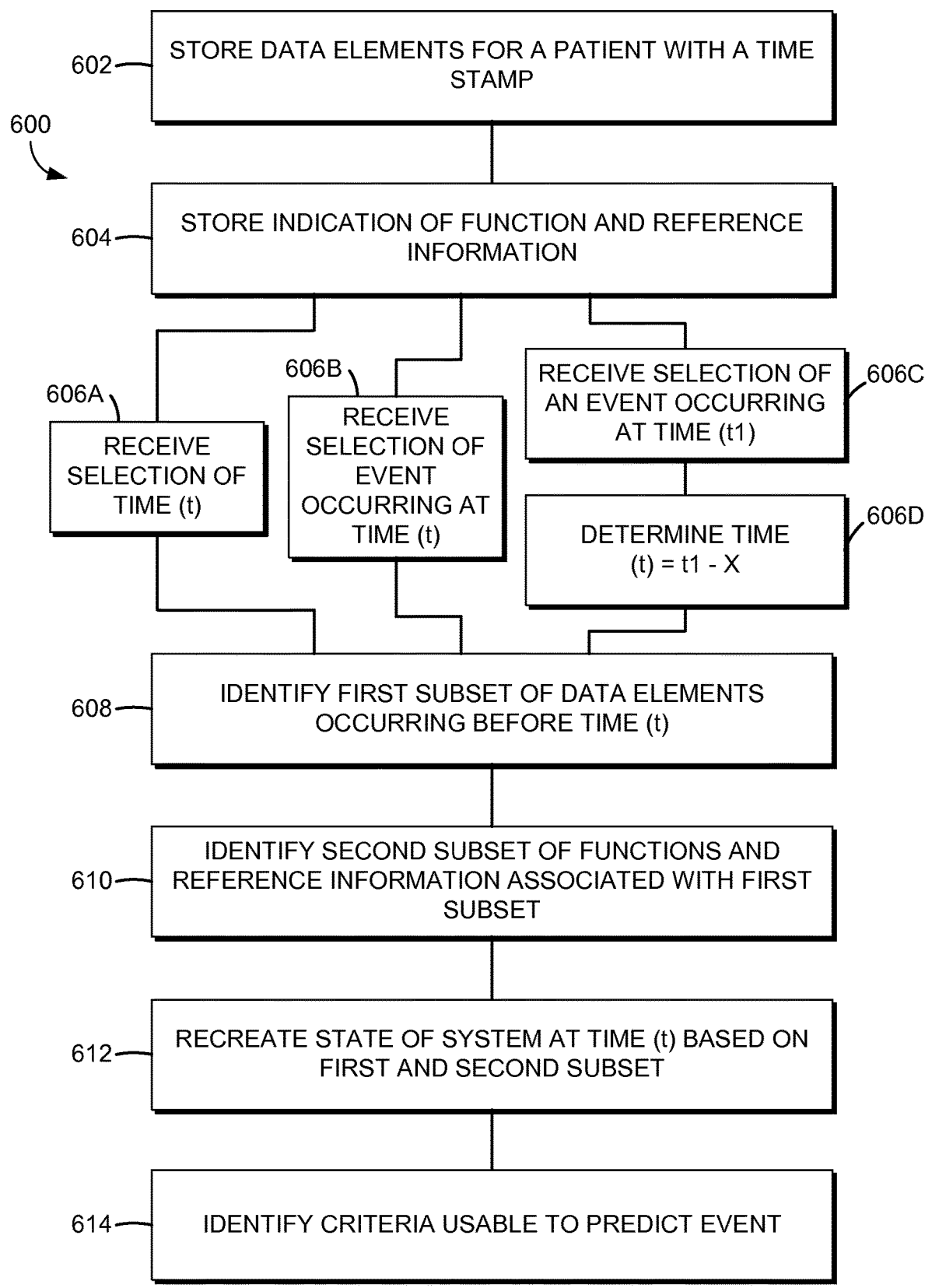
FIG. 6 is a flow diagram depicting a method for recreating a state of a system at a prior time in accordance with an embodiment of the invention.

With reference now to FIG. 6, a method 600 for recreating a state of a clinical system at a prior time in accordance with an embodiment of the invention is described. At a step 602, data elements associated with a patient are received or collected and are stored with a time stamp. The data elements are collected or received by the system from any available source including for example manual entry of data into the patient's electronic medical record (EMR), collection of data by monitoring devices, scanners and x-ray machines, clinician's notes and receipt of test results from third party vendors among a variety of others.

The time stamp is provided for each of the data elements by the system or by a third party such as the third party vendor providing test results or a clinician entering the data into the patient's EMR. And an individual time stamp is provided for each data element or is provided for a group of data elements. The time stamps are stored with the data elements in a database as metadata for the data elements or might be stored in a log file associated with the data elements.

Functions and reference information employed by the system are also stored, as indicated at a step 604. In an embodiment, the functions and reference information that are used in the treatment or care of the patient are stored in records associated with the patient. In another embodiment indications of the functions and reference information used in the care and treatment of the patient are stored in the patient's records while the functions and reference information are stored in elsewhere, such as in a general storage location, like the data store 24 of FIG. 1.

The functions and reference information are also provided with a time stamp and/or a version indicator. As the functions and reference information may be updated from time to time to a new version, the time stamp and/or version indicator indicates a version that is in use at a given time or time period. The time stamp and/or version indicator is stored with the patient's records, in a general storage and/or is indicated in a log file.

At a step 606A, a selection of a time (t) is received. The selection is received via, for example, a user interface, such as that depicted in FIGS. 3-5. The selection is received via manual entry of a time and date, selection of a time and date from a list, calendar or timeline or scrolling through a number of available times, among a variety of other methods. The selected time is any time within the period for which the patient was under the care and treatment of the clinical system or for which data is available for the patient. Or the selected time might be limited to instances in the care of the patient at which an event that was recognized by the system occurred.

Alternatively, at a step 606B a selection of an event is received. A selected time (t) is thus identified based on a time stamp associated with the selected event.

At a step 608, a subset of all of the data elements associated with a patient are identified. The data elements belonging to the subset are identified as those data elements that include a time stamp that occurs at or before the selected time (t), e.g. the time stamp of the data elements≤the selected time (t).

At a step 610, a subset of the functions and pieces of reference information that are associated with the data elements in the subset of data elements is identified. The functions and pieces of reference information include a time stamp that occurs prior to the selected time (t) and/or a version indicator that indicates that a particular version of the function or piece of reference information was in use at the selected time (t), e.g. the time stamp<the selected time (t).

In an embodiment, a version indicator indicates that a version of a function or piece of reference information that was in use at the time (t) is different than a current version. And a change log indicates modifications made to the function or piece of reference information between the selected time (t) and the current time. As such, the function or piece of reference information is "unmodified" based on the change log to provide the function or piece of reference information in its previous version for inclusion in the subset. In another embodiment, both a prior and a current version of the function or reference information is stored in a memory and, the appropriate version is provided for inclusion in the subset based on the associated time stamps or version indicators.

The state of the clinical system is recreated based on the subset of data elements and the subset of functions and pieces of reference information, as indicated at a step 612. In an embodiment, a user interface is provided to display one or more of the data elements, functions and pieces of reference information of the clinical system in its recreated state, such as that depicted in FIGS. 3-5. As such, the system may be viewed, audited, parsed or otherwise examined based on the data elements, functions and reference information that were available at the selected time (t).

The recreated state provides the functions and reference information in the appropriate versions thereof that were in use at the selected time (t). This allows the functions and reference information to be reviewed and executed or re-executed just as they would have been at the selected time (t). As such, changes or modifications to the functions and/or reference information that occurred after the selected time (t) will not affect the presentation or execution of those functions and/or pieces of reference information in the recreated state. This may allow analysis or auditing of any effects caused by the changes or modifications to the functions and/or pieces of reference information.

For example, assume a function for calculating the risk of a stroke in a patient was modified between a selected time (t) and a current time. Also assume that the patient had a stroke following the selected time (t). In such an instance, clinicians might question why an alert was not provided indicating the patient had a high risk of stroke. By recreating the state of the system at the selected time (t), the clinicians can analyze the patient's symptoms at the selected time (t). The clinicians might notice that the patient's symptoms should have caused the alert to be provided based on current recommendations and a current function used to provide such alerts. But the clinicians are also provided with an indication that a prior version of the function and/or reference information was in use at the selected time (t) and did not result in the provision of an alert. The clinicians might also re-execute the prior version of the function to determine that it was functioning properly.

In an embodiment, the clinicians are also enabled to select a subsequent, current or other version of the function or reference information for execution based on the data elements available at the selected time (t). This might provide an understanding of how changes or modifications to the function or reference information affects the output thereof.

In another embodiment, the state of the clinical system at a time prior to the occurrence of an event is analyzed to generate criteria useable to predict the occurrence of an event. As depicted in FIG. 6, a selection of an event occurring at a time (t1) is received, as indicated at a step 606C. A selected time (t) at which to recreate the state of the system is determined based on a predetermined period of time prior to the event, e.g. the selected time (t)=the time of the event (t1)–a predetermined period of time (X). The predetermined period of time is any desired amount of time, such as minutes, days, months, years, etc. The predetermined period of time might be selectable via a user interface by one or more of manual entry of a desired amount of time, a slider on a timeline or selection of an icon among a variety of other methods.

Following selection of the event, determination of the time (t) and re-creation of the state of the system as indicated at the step 612, criteria usable to predict the event are identified, as indicated at a step 614. The criteria include any identified data elements, functions and/or pieces of reference information that might indicate the impending or potential for the occurrence of the selected event. For example, the state of the system might be analyzed for a patient that suffered a heart attack—the heart attack being recorded as an event for the patient. The state of the system is recreated for a time occurring two hours prior to the heart attack event. The data elements available in the system two hours prior to the heart attack event indicate that a specific activity on the patient's electrocardiogram had steadily increased over the previous two days.

This increased activity might be identified as a criterion for predicting the onset of a heart attack. Similar data might also be analyzed for a plurality of other patients suffering heart attacks to confirm the findings. The state of the system at a time two hours prior to a heart attack event for each of those patients might also be recreated. And a new function might be generated for using this increased activity level as a predictor of heart attacks.

Figure 7:
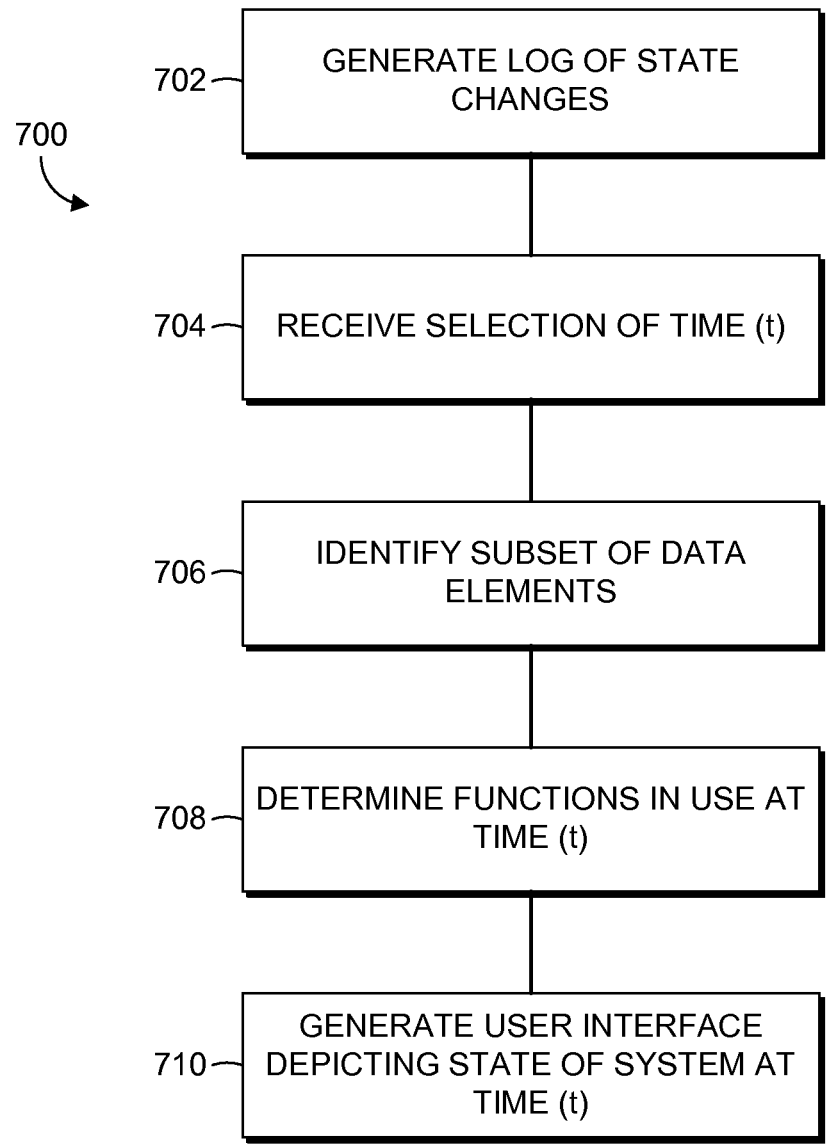
FIG. 7 is a flow diagram depicting a method for auditing a computing system to identify conditions of the computing system existing at a selected prior time in accordance with an embodiment of the invention.

With reference now to FIG. 7, a method 700 for auditing a computing system to identify conditions of the computing system existing at a selected prior time is described in accordance with an embodiment of the invention. At a step 702, a log is generated. The log includes a record of state changes to the computing system. The state changes comprise any mutations of data, functions or other elements of the computing system. The mutations are described in any level of detail sufficient to allow re-creation of the state of the system. For example, the mutations might be fully described in the log (e.g. value of x changed from x=a to x=b) or the log might include a pointer to a separate storage location that provides the details of the mutations. The log also includes an indication of the time when each of the state changes occurred.

At a step 704, a selection of a time (t) at which to recreate the state of the computing system is received. A subset of data elements are identified based at least in part on indications of the data elements that were available at the selected time (t) as provided by the log, as indicated at a step 706. Similarly, functions that were in use at the selected time (t) are identified based at least in part on the log, as indicated at a step 708. In an embodiment, the log provides an indication of a version of the functions in use at the selected time (t). And at a step 710, a user interface is generated depicting the state of the computing system at the selected time (t). The state of the computing system is recreated based on the identified data elements and functions available at the selected time (t) as indicated by the log.

As described previously, embodiments of the invention are described herein with respect to clinical systems, such as those in a hospital or other care facility. However, embodiments of the invention are not limited to such applications. For example, in the financial sector embodiments of the invention might be implemented to recreate the state of an electronic trading system for stocks and bonds. In such an instance, the state of the system at a selected time might be analyzed to determine why a stock purchase was or was not made. The state of the system might be recreated for the selected time and the data elements and functions associated with the stock purchase reviewed. In another embodiment, in a real estate system a transaction that is not in compliance with current regulations might be reviewed based on the state of the system at the time of the transaction. As such, it might be discovered that the reference information or functions associated with the regulations have changed since the time the transaction was made and that the transaction was in compliance with the regulations in force at that time.

Figure 8:
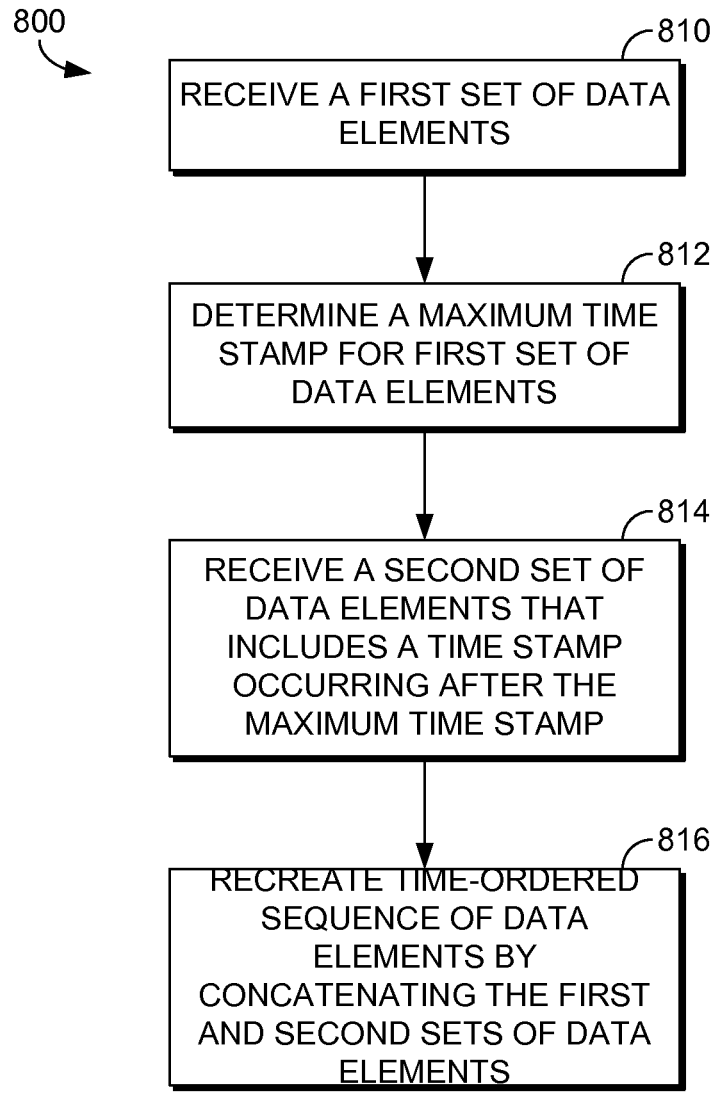
FIG. 8 is a flow diagram depicting a method for producing a time-ordered sequence of data elements in accordance with an embodiment of the invention.

With reference to FIG. 8, a flow diagram is depicted of an exemplary method 800 of producing a time-ordered sequence of data elements. At a step 810, a first set of data elements for a patient is received from a clinical system such as an electronic medical record system associated with a hospital or healthcare facility. The first set of data elements may be received subsequent to an extractor (such as, for example, the patient-data-tracking component 202 of FIG. 2) querying the clinical system and returning the set of data elements. In one aspect, the first set of data elements may comprise data elements returned on a first crawl of the clinical system. In another aspect, the first set of data elements may comprise data elements extracted on a subsequent crawl of the clinical system. The first set of data elements belongs to one or more clinical domains such as clinical documents, lab values, medications, problem lists, clinical orders, and the like. Further, each data element may comprise one or more state changes. By way of illustrative example, a data element may represent a physician note. The physician note may undergo a series of state changes. For example, the physician note may be added to the clinical system, updated a first time by the physician, and updated a second time by the physician. Each of these state changes is represented as a data element in the clinical system although they all refer to the same physician note.

Further, each data element within the first set of data elements is associated with a time stamp. Time stamping may be done by, for example, the patient-data-tracking component 202 of FIG. 2. The time stamp may be embedded as metadata in the data element and may represent a temporal time stamp or a logical sequencing time stamp. Time stamps may be associated with state changes for a given data element as well as associated with different data elements (physician note by physician A, physician note by physician B, etc.) in the clinical domain.

At a step 812, a maximum time stamp for the first set of data elements is determined. The maximum time stamp may represent the most recent state change within the first set of data elements. Using the example given above regarding the physician note that was added to the clinical system and updated twice by the physician, the maximum time stamp associated with the physician note would be that associated with the second update by the physician (e.g., the most recent update).

At a step 814, a second or subsequent set of data elements for the patient is received from the clinical system. Each data element in the subsequent set includes a time stamp occurring after the preceding or first set's respective maximum time stamp. At a step 816, a first time-ordered sequence of data elements is recreated by concatenating in sequential order the first set of data elements and the subsequent or second set of data elements. The time-ordered sequence of data elements is communicated to various clinical applications for further processing.

The method 800 is repeated in an iterative manner. For example, a maximum time stamp for the second set of data elements is determined. A third set of data elements for the patient is received from the clinical system. Each data element in the third set of data elements includes a time stamp occurring after the maximum time stamp for the second set of data elements. A second time-ordered sequence of data elements is recreated by concatenating the first set of data elements, the second set of data elements, and the third set of data elements. The end result is a complete, comprehensive view of the history of the data elements in the clinical system.

Figure 9:
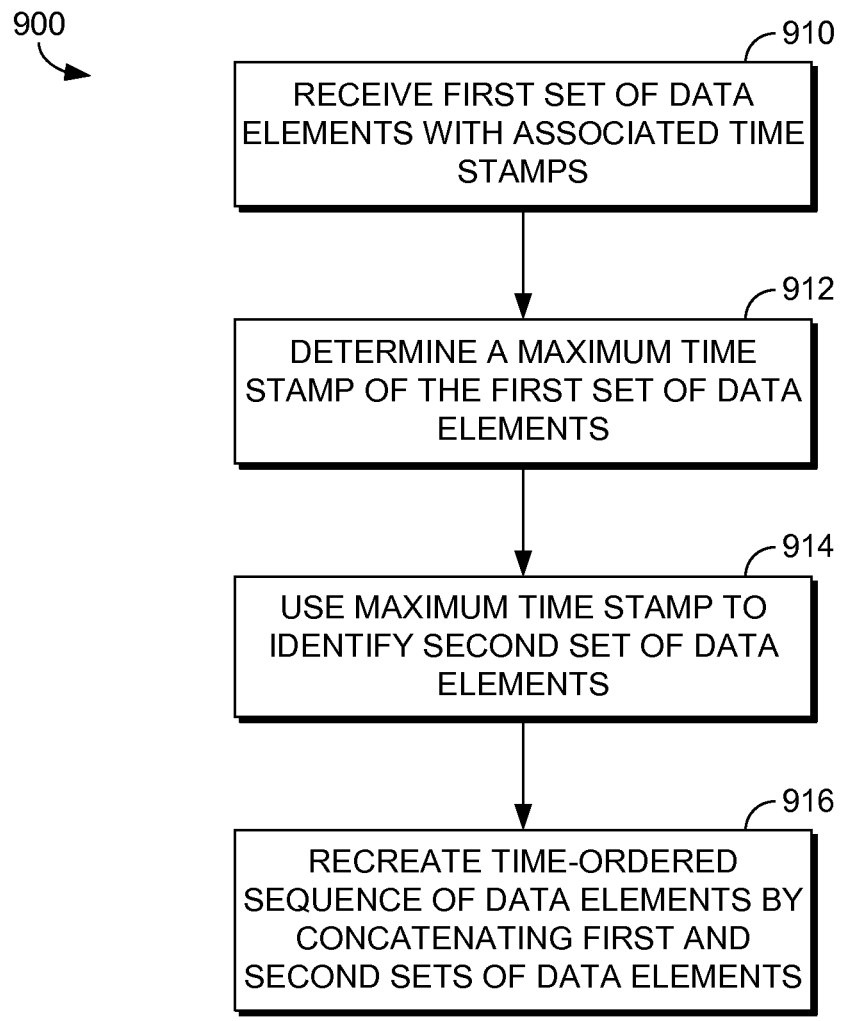
FIG. 9 is a flow diagram depicting a method for recreating a time-ordered sequence of data elements in accordance with an embodiment of the invention.

Turning now to FIG. 9, a flow diagram is depicted of an exemplary method 900 of recreating a time-ordered sequence of data elements in a clinical system. At a step 910, at a first point in time, a first set of data elements is received for a patient from a clinical system such as an electronic medical record system associated with a first hospital or healthcare facility. The data elements have undergone one or more mutations or state changes. For example, the data elements may have been added, modified, or deleted. Further, each data element in the first set of data elements is associated with a time stamp. The time stamp may represent a temporal time stamp or a logical sequencing time stamp.

At a step 912, a maximum time stamp is determined for the first set of data elements; the maximum time stamp represents the most recent state change associated with the data elements in the set of data elements. At a step 914, the maximum time stamp is used at a second point in time to identify a second set of data elements for the patient. Each data element in the second set of data elements has a respective time stamp after the maximum time stamp. The second point in time represents a point in time after the first point in time as measured by an independent clock.

At a step 916, a time-ordered sequence of data elements is recreated by concatenating the first and second sets of data elements. The first and second sets of data elements are concatenated in sequence such that the subsequent set of data elements (e.g., the second set of data elements) includes respective time stamps that occur after the maximum time stamp associated with the previous set of data elements (e.g., the first set of data elements). The method 900 is carried out iteratively to generate a comprehensive, time-ordered sequence of data elements.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. Non-transitory computer-readable media having computer-executable instructions embodied thereon that, when executed, perform a method for recreating a state of a clinical computing system, such that the method is useful in computer-driven disease surveillance systems, the method comprising:

extracting a first set of data elements for a patient occurring at or before a heart attack event or a stroke event from the clinical computing system, wherein the first set of data elements represents one of a clinical document, a lab value, a medication, a problem list, or a clinical order, and wherein first state changes that occur for each data element in the first set of data elements are identified, the first state changes comprising a mutation of data, function, or other computing element, and wherein the state changes are associated with the one of the clinical document, the lab value, the medication, the problem list, or the clinical order;

extracting a second set of data elements for the patient from the clinical computing system that were available in the clinical computing system prior to the heart attack event or the stroke event, wherein second state changes that occur for each data element in the second set of data elements are identified, wherein the second set of data elements represents one of the clinical document, the lab value, the medication, the problem list, or the clinical order, the second state changes comprising a mutation of data, function, or other computing element, and wherein the second state changes are associated with the one of the clinical document, the lab value, the medication, the problem list, or the clinical order;

recreating, via a computing device having a processor and a memory, the state of the clinical computing system by concatenating the first set of data elements and the second set of data elements to determine differences between the first state changes and the second state changes;

based at least in part on recreating the state of the clinical computing system, identifying criteria to predict an occurrence of the heart attack event or the stroke event; and communicating for display on a computer interface a recreated state of the clinical computing system and the criteria to predict the occurrence of the heart attack event or the stroke event for the patient, wherein the recreated state of the clinical computing system is prior to the heart attack event or the stroke event, and wherein the first set of data elements and the second set of data elements indicate a specific activity on an electrocardiogram of the patient increased over a predetermined activity level prior to the heart attack event or the stroke event.

2. The media of claim 1, wherein the first and second sets of data elements belong to a clinical domain comprising the one of the clinical document, the lab value, the medication, the problem list, or the clinical order.

3. The media of claim 2, wherein the clinical domain is represented by a logical representation of data.

4. The media of claim 1, wherein each data element of the first set of data elements and the second set of data elements have a time stamp that represents either a temporal measurement or a logical sequencing.

5. The media of claim 4, further comprising:

determining a second data element in the second set of data elements that has a largest value of time stamp as compared to the remaining data elements in the second set of data elements;

receiving a third set of data elements for the patient from the clinical computing system available in the clinical computing system, each data element in the third set of data elements having an associated time stamp embedded as metadata, the third set of data elements representing the one of the clinical document, the lab value, the medication, the problem list, or the clinical order, wherein third state changes that occur for the each data element in the third set of data elements are identified, the third state changes comprising a mutation of data, function, or other computing element, and wherein the third state changes are associated with the one of the clinical document, the lab value, the medication, the problem list, or the clinical order;

recreating, via the computing device having the processor and the memory, an additional state of the clinical computing system by comparing the first set of data elements, the second set of data elements, and the third set of data elements to determine differences among the first state changes, the second state changes, and the third state changes; and communicating for display on the computer interface the additional state of the clinical computing system and updated criteria.

6. The media of claim 1, further comprising:

communicating the recreated state of the clinical computing system to a first application for processing.

7. The media of claim 6, wherein the first application is a clinical application.

8. The media of claim 1, wherein the recreated state of the clinical computing system is two hours prior to the heart attack event, and wherein the first set of data elements and the second set of data elements indicate the specific activity on the electrocardiogram of the patient steadily increased over two days prior to the heart attack event.

9. The media of claim 8, wherein the specific activity is analyzed for a plurality of other patients suffering heart attacks.

10. A system for recreating a state of a clinical computing system comprising one or more computing devices having a processor and a memory and configured to provide:

a knowledge-base-tracking component for identifying state changes associated with data elements, wherein the state changes comprise a mutation of data, function, or other computing element;

a patient-data-tracking component configured to identify and extract a plurality of sets of data elements associated with a patient that were available in the clinical computing system before a blood flow event, wherein the plurality of sets of data elements represent one of a clinical document, a lab value, a medication, a problem list, or a clinical order, and wherein the plurality of sets of data elements comprises the state changes, and wherein the state changes are associated with the one of the clinical document, the lab value, the medication, the problem list, or the clinical order; and an auditing component configured to recreate the state of the clinical computing system before the blood flow event by concatenating each of the state changes of each data element in the plurality of sets of data elements, and identify criteria based at least in part on each of the state changes to predict other occurrences of the blood flow event, wherein the plurality of sets of data elements in the clinical computing system before the blood flow event indicate a specific measurement of the patient increased over a predetermined activity level prior to the blood flow event.

11. The system of claim 10, further comprising:
a scheduling component configured to invoke the patient-data-tracking component at preset intervals.

12. The system of claim 10, wherein the patient-data-tracking component comprises an extractor.

13. The system of claim 12, wherein the extractor is configured to query a plurality of clinical systems.

14. The system of claim 13, wherein the plurality of clinical systems are disparate clinical systems, and wherein the knowledge-base-tracking component further comprises a version indicator for the identifying the state changes, wherein the version indicator indicates a version of a data element at a particular time.

15. A computer-implemented method executed by a computing device having one or more processors for recreating a state of a clinical computing system, such that the method is useful in computer-driven disease surveillance systems, the method comprising:

extracting from the clinical computing system a first set of data elements for a patient occurring at or before a blood flow event, the first set of data elements representing one of a clinical document, a lab value, a medication, a problem list, or a clinical order, wherein the first set of data elements comprises a first state change comprising a mutation of data, function, or other computing element, and wherein the first state change is associated with the one of the clinical document, the lab value, the medication, the problem list, or the clinical order;

extracting from the clinical computing system a second set of data elements for the patient that were available in the clinical computing system prior to the blood flow event, the second set of data elements representing the one of the clinical document, the lab value, the medication, the problem list, or the clinical order, wherein the second set of data elements comprises a second state change comprising a mutation of data, function, or other computing element, and wherein the second state change is associated with the one of the clinical document, the lab value, the medication, the problem list, or the clinical order that occurred before or during the blood flow event;

recreating the state of the clinical computing system before or during the blood flow event by concatenating the first and second sets of data elements to determine differences between the first state change and the second state change;

based at least in part on recreating the state of the clinical computing system, identifying criteria to predict an occurrence of the blood flow event; and communicating for display on a computer interface a recreated state of the clinical computing system before or during the blood flow event and the criteria to predict the occurrence of the blood flow event for the patient, wherein the first set of data elements and the second set of data elements indicate a specific activity of the patient increased over a predetermined activity level prior to the blood flow event.

16. The method of claim 15, wherein the clinical computing system comprises an electronic medical record system.

17. The method of claim 15, wherein the first state change and the second state change comprise at least one of addition of information, deletion of information, or modification of information.

18. The method of claim 15, wherein each data element of the first set of data elements and the second set of data elements have a time stamp, and the time stamp for a data element of the first set of data elements has a largest value of time stamp that represents a most recent state change.

19. The method of claim 15, wherein the state of the clinical computing system is utilized by one or more clinical applications.

20. The method of claim 15, wherein the blood flow event is a stroke or a heart attack.

* * * * *